(12) United States Patent
Matsuda et al.

(10) Patent No.: US 9,358,246 B2
(45) Date of Patent: Jun. 7, 2016

(54) READTHROUGH INDUCING AGENT AND DRUG FOR TREATING GENETIC DISEASE CAUSED BY NONSENSE MUTATION

(71) Applicants: Microbial Chemistry Research Foundation, Tokyo (JP); University of Tokyo, Tokyo (JP)

(72) Inventors: Ryoichi Matsuda, Tokyo (JP); Masataka Shiozuka, Tokyo (JP); Akira Wagatsuma, Tokyo (JP); Yoshikazu Takahashi, Tokyo (JP); Daishiro Ikeda, Tokyo (JP); Yoshiaki Nonomura, Tokyo (JP); Masafumi Matsuo, Hyogo (JP); Atsushi Nishida, Hyogo (JP)

(73) Assignees: Microbial Chemistry Research Foundation, Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 14/486,321

(22) Filed: Sep. 15, 2014

(65) Prior Publication Data

US 2015/0005249 A1    Jan. 1, 2015

Related U.S. Application Data

(63) Continuation of application No. 13/563,872, filed on Aug. 1, 2012, now abandoned, which is a continuation of application No. PCT/JP2011/052263, filed on Feb. 3, 2011.

(30) Foreign Application Priority Data

Feb. 3, 2010    (JP) ................. 2010-021817

(51) Int. Cl.
A61K 31/7036    (2006.01)
C07H 15/234    (2006.01)
A61K 48/00    (2006.01)

(52) U.S. Cl.
CPC .......... *A61K 31/7036* (2013.01); *C07H 15/234* (2013.01); *A61K 48/00* (2013.01)

(58) Field of Classification Search
CPC ................................................ A61K 31/7036
See application file for complete search history.

(56) References Cited

U.S. PATENT DOCUMENTS

| 5,488,038 | A  | 1/1996 | Kondo et al. |
|---|---|---|---|
| 2005/0014835 | A1 | 1/2005 | Arakawa et al. |
| 2005/0153906 | A1 | 7/2005 | Bedwell et al. |
| 2009/0093418 | A1 | 4/2009 | Bassov et al. |
| 2010/0069455 | A1 | 3/2010 | Takato et al. |
| 2010/0210578 | A1 | 8/2010 | McLean et al. |

FOREIGN PATENT DOCUMENTS

| CN | 1843330 A | 10/2006 |
|---|---|---|
| EP | 2062585 | 5/2009 |
| JP | 2004522763 | 7/2004 |
| JP | 2008079510 | 4/2008 |
| JP | 2008161075 | 7/2008 |
| JP | 2009095436 | 5/2009 |
| JP | 2009523775 | 6/2009 |
| JP | 2009532461 | 9/2009 |
| JP | 2009255077 | 11/2009 |
| WO | 02102361 | 12/2002 |
| WO | 2007/083094 | 1/2007 |
| WO | 2008023462 | 2/2008 |
| WO | 2009019504 | 2/2009 |

OTHER PUBLICATIONS

Barton-Davis et al., J. Clin. Invest., 1999, 104, p. 375-381.*
Nudelman et al., J. Med. Chem., 2009, 52, p. 2836-2845.*
Hainrichson et al., Org. Biomol. Chem., 6 (2008) pp. 227-239.
Shiozuka, Masataka et al., "Readthrough Therapy for Muscular Dystrophy," Seitai no Kagaku (Science of the Living Body), 62(2) (2011) pp. 134-137.
Politano, L., et al., "Gentamicin administration in Duchenne patients with premature stop codon. Preliminary results," Acta. Myologica, vol. XXII (2003) pp. 15-21.
Wilschanski, M.D., M. et al., "Gentamicin-Induced Correction of CFTR Function in Patients with Cystic Fibrosis and CFTR Stop Mutations," The New England Journal of Medicine, vol. 349 (Oct. 9, 2003) pp. 1433-1441.
Manuvakhova, M., et al., "Aminoglycoside antibiotics mediate context-dependent suppression of termination codons in a mammalian translation system," RNA, vol. 6 (2000) pp. 1044-1055.
Tanaka et al., Mechanism of Action of Habekacin, a Novel Amino Acid-Containing Aminoglycoside Antibiotic, Antimicrobial Agents and Chemotherapy, vol. 24, No. 5 (Nov. 1983), pp. 797-802.
https://pubchem.ncbi.nlm.nih.gov/substance/12012746#section=Top Available Date Jul. 28, 2006.

* cited by examiner

*Primary Examiner* — Jonathan S Lau
(74) *Attorney, Agent, or Firm* — Carmody Torrance Sandak & Hennessey LLP (57) ABSTRACT

A readthrough inducing agent for inducing readthrough of a premature stop codon generated by nonsense mutations, the readthrough inducing agent comprising a compound having a structure expressed by the following Structural Formula (A), and a drug for treating a genetic disease caused by nonsense mutations, the drug comprising the readthrough inducing agent.

Structural Formula (A)

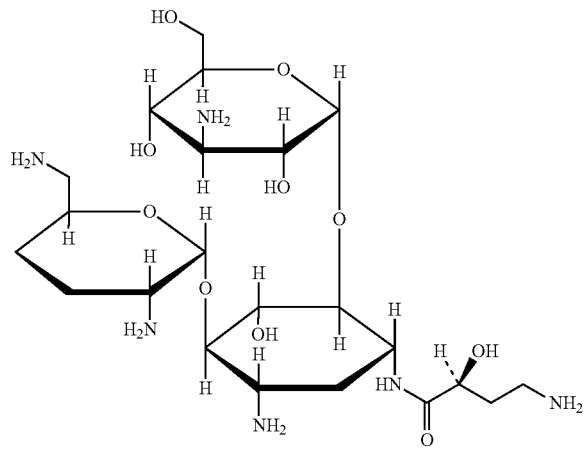

6 Claims, 5 Drawing Sheets

READTHROUGH INDUCING AGENT AND DRUG FOR TREATING GENETIC DISEASE CAUSED BY NONSENSE MUTATION

CROSS REFERENCE TO RELATED APPLICATIONS

This is a continuation of application Ser. No. 13/563,872 filed on Aug. 1, 2012, which is a continuation application of PCT/JP2011/052263, filed on Feb. 3, 2011.

BACKGROUND OF THE INVENTION

1. Field of the Invention

The present invention relates to: a readthrough inducing agent for inducing readthrough of a premature stop codon generated due to nonsense mutations; and a drug for treating a genetic disease caused by nonsense mutations.

2. Description of the Related Art

In the genetic disease caused by nonsense mutations, protein expression is inhibited due to the premature stop codon generated by a point mutation on a gene. Examples of the genetic disease caused by nonsense mutations include muscular dystrophy, multiple sclerosis, infantile neuronal ceroid lipofuscinosis, Alzheimer's disease, Tay-Sachs disease, neural tissue degeneration, Parkinson's disease, chronic rheumatoid arthritis, graft versus host disease, arthritis, hemophilia, von Willebrand disease, ataxia-telangiectasia, thalassemia, nephrolithiasis, osteogenesis imperfecta, cirrhosis, neurofibroma, bullous disease, lysosomal storage disease, Hurler's disease, familial cholesterolemia, cerebellar ataxia, tuberous sclerosis, familial erythrocytosis, immune deficiency, kidney disease, lung disease, cystic fibrosis, familial hypercholesterolemia, pigmentary retinopathy, amyloidosis, atherosclerosis, gigantism, dwarfism, hypothyroidism, hyperthyroidism, aging, obesity, diabetes mellitus, Niemann-Pick disease, Marfan syndrome, and cancer.

For example, Duchenne muscular dystrophy arises from the lack of dystrophin protein in sarcolemma. In this disease, a stop codon is generated (premature stop codon) due to the mutation on the muscular dystrophy gene located on X chromosome, and translation is interrupted or terminated at the mutation site. Thus, normal expression of dystrophin and dystrophin-associated proteins is inhibited and as a result, patients who suffer from this disease lack dystrophin proteins.

For treating such genetic disease caused by nonsense mutations, a method employing a compound having readthrough activity has been attempted. The readthrough activity means that when a specific compound is administered to patients who have a premature stop codon generated by nonsense mutations and lack a specific protein, the above-mentioned compound acts on a ribosome and the ribosome reads through the stop codon and continues translation. As a result of readthrough, wild-type normal proteins are synthesized.

An aminoglycoside antibiotic, gentamicin and a dipeptide antibiotic, negamycin are known exemplary compounds having such readthrough activity.

Regarding gentamicin, Politano et al. has found that administration of gentamicin to patients with Duchenne muscular dystrophy led to the accumulation of dystrophin protein (see, for example, Acta. Myol. 2003, Vol. 22, pp. 15-21). In addition, it is reported that topical administration of gentamicin to the respiratory epithelium of patients with cystic fibrosis can correct typical electrophysiological abnormalities (see, for example, N. Engl. J. Med. 2003, Vol. 349, pp. 1433-1441). Furthermore, clinical trials of gentamicin have been conducted in the United States as a therapy for genetic diseases. However, there is concern for high toxicity of gentamicin. Since long-term administration is required, gentamicin is not a satisfactory therapeutic agent for the patients of genetic disease caused by nonsense mutations.

Regarding negamycin, it is confirmed that administration of the compound to muscular dystrophy model mice restores dystrophin expression (see, for example, International Publication No. WO 2002/102361). However, negamycin is an unapproved drug. There is an immediate need for a drug against genetic diseases caused by nonsense mutations. Thus, negamycin is not realistic as a therapeutic drug for genetic diseases caused by nonsense mutations.

In addition, clinical trial of ataluren (PTC124), which has readthrough activity, has been conducted in the United States as a drug for, for example, Duchenne muscular dystrophy. However, the trial is stopped at phase III at present. As mentioned above, a drug against genetic diseases caused by nonsense mutations is needed immediately. Thus, ataluren is not realistic as a therapeutic drug for genetic diseases caused by nonsense mutations.

In view of the above, demand has arisen for prompt development of a readthrough inducing agent that contains a compound having low toxicity and readthrough activity and of a drug for treating a genetic disease caused by nonsense mutations.

SUMMARY OF THE INVENTION

The present invention aims to solve the above existing problems and to achieve the following object. An object of the present invention is to provide: a readthrough inducing agent that comprises a compound having low toxicity and readthrough activity; and a drug for treating a genetic disease caused by nonsense mutations, the drug comprising the readthrough inducing agent.

As a result of the diligent studies conducted by the present inventors to solve the above problems, the present inventors have found that a compound having a structure expressed by the following Structural Formula (A) (hereinafter may be referred to as "arbekacin"), which is used as a specific drug against infectious disease caused by MRSA, has excellent readthrough activity and have completed the invention of the present application.

Structural Formula (A)

The present invention is based on the above finding obtained by the present inventors. A readthrough inducing agent of the present invention for inducing readthrough of a premature stop codon generated by nonsense mutations as a means for solving the above existing problems includes a compound having a structure expressed by the following Structural Formula (A).

Structural Formula (A)

The present invention can provide: a readthrough inducing agent comprising a compound having low toxicity and readthrough activity; and a drug for treating a genetic disease caused by nonsense mutations, the drug comprising the readthrough inducing agent.

DETAILED DESCRIPTION OF THE INVENTION (Readthrough Inducing Agent)

A readthrough inducing agent of the present invention contains at least a compound having a structure expressed by the following Structural Formula (A) and, if necessary, further contains other ingredients.

Structural Formula (A)

The readthrough means that when one base is substituted due to a point mutation on a gene and a premature stop codon is generated upstream of the normal translation termination site, the premature stop codon is read through and translation continues to the normal translation termination site. The readthrough of the premature stop codon enables the synthesis of functional full-length protein.

<Compound Having a Structure Expressed by Structural Formula (A) (Arbekacin)>

Arbekacin (1-N-AHB-dibekacin) is a compound, in which a 4-amino-2-hydroxybutyryl (AHB) group is added to dibekacin (3',4'-deoxykanamycin B), and arbekacin has been used as a specific drug against infectious disease caused by MRSA since the end of 1990.

The arbekacin may be in the form of salt or in the form of solvate.

The salt is not particularly limited and may be suitably selected according to the intended purpose. Examples thereof include hydrohalic acid salts, inorganic acid salts, carboxylates, amino acid salts, and organic acid salts. Among these, inorganic acid salts are preferable.

Specific examples of the hydrohalic acid salt include hydrofluoride, hydrochloride, hydrobromate, and hydroiodide.

Specific examples of the inorganic acid salt include sulfates, nitrates, phosphates, perchlorates, and carbonates. Among these, sulfates are preferable.

Specific examples of the carboxylate include acetates, trichloroacetates, trifluoroacetates, hydroxyacetates, lactates, citrates, tartrates, oxalates, benzoates, mandelates, butyrates, maleates, propionates, formates and malates.

Specific examples of the amino acid salt include alginates, aspartates and glutamates.

Specific examples of the organic acid salt include methanesulfonates and p-toluenesulfonates.

The solvate is not particularly limited and may be suitably selected according to the intended purpose. Examples thereof include hydrates and ethanolates.

The arbekacin may be synthesized by chemical synthesis or commercially available products may be used.

The synthesis method of arbekacin is not particularly limited and may be suitably selected according to the intended purpose. Examples thereof include the method described on page 412 in The Journal of Antibiotics, Vol. 26, 1973.

Examples of the commercially available arbekacin include habekacin (product of Meiji Seika Pharma Co., Ltd).

The production methods of the salt of arbekacin and the solvate of arbekacin are not particularly limited and may be suitably selected from commonly known methods.

Arbekacin may be derivatives thereof.

The amount of arbekacin in the readthrough inducing agent is not particularly limited and may be suitably selected according to the intended purpose. The readthrough inducing agent may be arbekacin itself.

<Other Ingredient>

The other ingredient in the readthrough inducing agent is not particularly limited and may be suitably selected according to the intended purpose. Examples thereof include pharmacologically acceptable carriers.

The pharmacologically acceptable carrier is not particularly limited and may be suitably selected according to the intended purpose. Examples thereof include ethanol, water and starch.

The amount of the other ingredients contained in the readthrough inducing agent is not particularly limited, so long as the effects of arbekacin are not impaired, and may be suitably selected according to the intended purpose.

<Use>

The readthrough inducing agent may be used alone or in combination with a drug containing other active ingredients. Also, the readthrough inducing agent may be incorporated before use into a drug containing other active ingredients.

As shown in Test Examples 1 to 8 to be described below, the readthrough inducing agent has low toxicity and excellent readthrough activity because it contains arbekacin.

Accordingly, the readthrough inducing agent can be suitably used for the treatment of genetic diseases caused by nonsense mutations.

<Dosage Form>

The dosage form of the readthrough inducing agent is not particularly limited and may be suitably selected according to the intended purpose. Examples of the dosage form include liquids, powder, capsules, and tablets. The readthrough inducing agent can be formed into each of these dosage forms by a routine method.

<Administration>

The administration method of the readthrough inducing agent is not particularly limited and may be suitably selected depending on, for example, the dosage form of the readthrough inducing agent. The readthrough inducing agent can be administered orally or parenterally.

The dose of the readthrough inducing agent is not particularly limited and may be suitably selected considering various factors of target individuals such as their age, body weight, constitution, symptoms and concomitant use of a drug containing other active ingredients. The dose of the readthrough inducing agent can be, for example, in terms of the amount of the compound having a structure expressed by Structural Formula (A) (arbekacin), 0.1 mg/kg/day to 300 mg/kg/day, preferably 0.5 mg/kg/day to 50 mg/kg/day.

The timing of administration of the readthrough inducing agent is not particularly limited and may be suitably selected according to the intended purpose.

The animal species to which the readthrough inducing agent is administered is not particularly limited and may be suitably selected according to the intended purpose. Particularly suitable examples thereof include human.

Preferably, before the administration of the readthrough inducing agent, a biological sample is collected from an individual and the presence or absence of a premature stop codon in the gene contained in the biological sample is examined, and the readthrough inducing agent is administered to the individual from which the premature stop codon has been detected. The method for examining the presence or absence of a premature stop codon is not particularly limited and may be suitably selected from known methods. Examples thereof include Southern blotting, polymerase chain reaction (PCR), short tandem repeat (STR), and restriction fragment length polymorphism (RFLP).

(Drug for Treating a Genetic Disease Caused by Nonsense Mutations)

A drug for treating a genetic disease caused by nonsense mutations of the present invention contains at least the readthrough inducing agent and, if necessary, further contains other ingredients.

<Genetic Disease Caused by Nonsense Mutations>

The genetic disease caused by nonsense mutations is a disease in which one base is substituted due to a point mutation on a gene and a premature stop codon is generated upstream of the normal translation termination site, causing the inhibition of the expression of functional full-length protein.

Specific examples of the genetic disease caused by nonsense mutations include muscular dystrophy, multiple sclerosis, infantile neuronal ceroid lipofuscinosis, Alzheimer's disease, Tay-Sachs disease, neural tissue degeneration, Parkinson's disease, chronic rheumatoid arthritis, graft versus host disease, arthritis, hemophilia, von Willebrand disease, ataxia-telangiectasia, thalassemia, nephrolithiasis, osteogenesis imperfecta, cirrhosis, neurofibroma, bullous disease, lysosomal storage disease, Hurler's disease, familial cholesterolemia, cerebellar ataxia, tuberous sclerosis, familial erythrocytosis, immune deficiency, kidney disease, lung disease, cystic fibrosis, familial hypercholesterolemia, pigmentary retinopathy, amyloidosis, atherosclerosis, gigantism, dwarfism, hypothyroidism, hyperthyroidism, aging, obesity, diabetes mellitus, Niemann-Pick disease, Marfan syndrome, and cancer. Among these, suitable examples thereof include muscular dystrophy and particularly suitable examples thereof include Duchenne muscular dystrophy.

The amount of the readthrough inducing agent in the drug for treating a genetic disease caused by nonsense mutations is not particularly limited and may be suitably selected according to the intended purpose. The drug for treating a genetic disease caused by nonsense mutations may be the readthrough inducing agent itself.

<Other Ingredient>

The other ingredient in the drug for treating a genetic disease caused by nonsense mutations is not particularly limited and may be suitably selected according to the intended purpose. Examples thereof include pharmacologically acceptable carriers.

The pharmacologically acceptable carrier is not particularly limited and may be suitably selected according to the intended purpose. Examples thereof include ethanol, water and starch.

The amount of the other ingredients contained in the drug for treating a genetic disease caused by nonsense mutations is not particularly limited, so long as the effects of arbekacin are not impaired, and may be suitably selected according to the intended purpose.

<Use>

The drug for treating a genetic disease caused by nonsense mutations may be used alone or in combination with a drug containing other active ingredients. Also, the drug for treating a genetic disease caused by nonsense mutations may be incorporated before use into a drug containing other active ingredients.

As shown in Test Examples 1 to 8 to be described below, the drug for treating a genetic disease caused by nonsense mutations has low toxicity and excellent readthrough activity because it contains the readthrough inducing agent.

Accordingly, the drug for treating a genetic disease caused by nonsense mutations can be suitably used for the treatment of genetic diseases caused by nonsense mutations.

<Dosage Form>

The dosage form of the drug for treating a genetic disease caused by nonsense mutations is not particularly limited and may be suitably selected according to the intended purpose. Examples of the dosage form include liquids, powder, capsules, and tablets. The drug for treating a genetic disease caused by nonsense mutations can be formed into each of these dosage forms by a routine method.

<Administration>

The administration method of the drug for treating a genetic disease caused by nonsense mutations is not particularly limited and may be suitably selected depending on, for example, the dosage form of the drug for treating a genetic disease caused by nonsense mutations. The drug for treating a genetic disease caused by nonsense mutations can be administered orally or parenterally.

The dose of the drug for treating a genetic disease caused by nonsense mutations is not particularly limited and may be suitably selected considering various factors of target individuals such as their age, body weight, constitution, symptoms and concomitant use of a drug containing other active ingredients. The dose of the drug for treating a genetic disease caused by nonsense mutations can be, for example, in terms of the amount of the compound having a structure expressed by Structural Formula (A) (arbekacin), 0.1 mg/kg/day to 300 mg/kg/day, preferably 0.5 mg/kg/day to 50 mg/kg/day.

The timing of administration of the drug for treating a genetic disease caused by nonsense mutations is not particularly limited and may be suitably selected according to the intended purpose.

The animal species to which the drug for treating a genetic disease caused by nonsense mutations is administered is not particularly limited and may be suitably selected according to the intended purpose. Particularly suitable examples thereof include human.

Preferably, before the administration of the drug for treating a genetic disease caused by nonsense mutations, a biological sample is collected from an individual and the presence or absence of a premature stop codon in the gene contained in the biological sample is examined, and the drug for treating a genetic disease caused by nonsense mutations is administered to the individual from which the premature stop codon has been detected. The method for examining the presence or absence of a premature stop codon is not particularly limited and may be suitably selected from known methods. Examples thereof include Southern blotting, polymerase chain reaction (PCR), short tandem repeat (STR), and restriction fragment length polymorphism (RFLP).

(Treatment Method)

Since the drug for treating a genetic disease caused by nonsense mutations contains the readthrough inducing agent, administration of the drug for treating a genetic disease caused by nonsense mutations to an individual having a genetic disease caused by nonsense mutations enables treatment of the individual having a genetic disease caused by nonsense mutations. Therefore, the present invention also relates to a method for treating an individual having a genetic disease caused by nonsense mutations, the method comprising administering the drug for treating a genetic disease caused by nonsense mutations to the individual.

EXAMPLES

The present invention will next be described in detail by way of Test Examples, which should not be construed as limiting the present invention thereto.

Test Example 1

Analysis of Readthrough Activity

<Production of Transgenic Mice for Detection of Readthrough Activity>

In order to analyze in vivo readthrough activity, transgenic mice for detection of readthrough activity (Readthrough Evaluation and Assessment by Dual-reporter mice (hereinafter may be referred to as "R.E.A.D. mice")) were produced in the same manner as described in the paragraphs [0071] to [0083] of International Publication No. WO 2008/004610.

In the R.E.A.D. mice, an expression vector (pCAGGS) is introduced into the germline. pCAGGS contains a cytomegalovirus enhancer/chicken β-actin hybrid promoter and a construct in which β-galactosidase gene and luciferase gene are connected with premature stop codon (TGA) (27 mer containing the surrounding 12 mer sequence before and after the premature stop codon of the exon 23 of the mdx mice). In the produced R.E.A.D. mice, only β-galactosidase is typically expressed, but readthrough of premature stop codon results in the expression of luciferase.

<Evaluation of Readthrough Activity>

The compounds listed in Table 1 below were subcutaneously injected to three groups of female littermate R.E.A.D. mice (one group of 8-week-old mice (7 mice) and two groups of 10-week-old mice (5 mice for each group) at the dose in Table 1 daily for 7 days.

Arbekacin (hereinafter may be referred to as "ABK") and gentamicin (hereinafter may be referred to as "GM") were used as the compound to be administered.

ABK bulk powder, supplied from Meiji Seika Pharma Co., Ltd., was used as arbekacin. Also, gentamicin was used for comparison.

Administration was performed by first diluting the compound to be administered with physiological salt solution (product of Otsuka Pharmaceutical Co., Ltd.) and then administrating 0.1 mL thereof.

Readthrough efficiency was determined as follows. After subcutaneous injection daily for 7 days, muscle tissue was excised. Using the extracts of the muscle tissue, β-galactosidase activity and luciferase activity were measured with a luminometer using luciferin-galactosidase and luciferin. The readthrough efficiency was obtained by dividing the luciferase activity measured by the β-galactosidase activity measured. In Table 1 below, the readthrough efficiency is expressed as a relative readthrough efficiency based on the readthrough efficiency when gentamicin was administered as 1.

TABLE 1

| Compound administered | Dose mg/day | Readthrough efficiency |
|---|---|---|
| GM | 0.5 | 1 |
| None (Physiological saline alone) | | 0.62 |
| ABK | 0.5 | 1.17 |
| ABK | 1 | 1.14 |
| ABK | 2 | 1.33 |
| ABK | 4 | 1.47 |

From the results in Table 1, it was confirmed that arbekacin (ABK) has readthrough activity. In addition, it was confirmed that the readthrough activity of arbekacin is higher than that of gentamicin (GM) which has been known to have readthrough activity.

Test Example 2

Toxicity Test

An injection solution (50 mg/1 mL) of habekacin (arbekacin sulfate), commercially available as arbekacin (ABK) from Meiji Seika Pharma Co., Ltd., was diluted with physiological salt solution (product of Otsuka Pharmaceutical Co., Ltd.) so that the doses of ABK would be those shown in the following Table 2, and 0.2 mL of each diluted solution was subcutaneously injected daily for 7 days to 10-week-old littermate R.E.A.D. mice (one male group (3 mice) and one female group (3 mice)).

Toxicity was evaluated as follows. The body weight was measured before and after the daily subcutaneous injection for 7 days and the toxicity was evaluated based on the change in body weight (average value of 6 mice).

The readthrough efficiency was calculated in the same manner as in Test Example 1. Specifically, β-galactosidase activity and luciferase activity were measured and the readthrough efficiency was obtained by dividing the luciferase activity measured by the β-galactosidase activity measured. In Table 2 below, the readthrough efficiency is expressed as a relative readthrough efficiency based on the readthrough efficiency when only physiological saline was administered as 1.

TABLE 2

| Compound administered | Dose mg/day | Readthrough efficiency | Change in body weight |
|---|---|---|---|
| None (Physiological saline alone) | | 1 | 102.5% (SD = 0.31) |
| ABK | 2.5 | 2.20 | 98.8% (SD = 0.38) |
| ABK | 5 | 1.50 | 96.9% (SD = 0.38) |
| ABK | 7.5 | — | — |

When ABK was administered in an amount of 7.5 mg/day, one mouse died 2 days after administration initiation (the body weight changed from 18.4 g to 17.3 g), and two mice died 3 days after administration initiation (the body weight of one mouse changed from 21.0 g to 19.0 g, and that of the other changed from 19.3 g to 18.2 g).

The results in Table 2 indicate that toxicity of arbekacin (ABK) is weak. That is, when a large amount of arbekacin (ABK), 7.5 mg/day, was administered, mice died, whereas when 2.5 mg/day or 5 mg/day, doses at which readthrough activity was observed, was administered, the decrease in body weight was small and weak toxicity was observed.

In addition, from $LD_{50}$ (50% Lethal Dose), toxicity of arbekacin is found to be weak. When gentamicin was intravenously injected to mice, $LD_{50}$ is approximately 76 mg/kg as can be found from the descriptions in the following: Development of Novel Aminoglycoside (NB54) with Reduced Toxicity and Enhanced Suppression of Disease-Causing Premature Stop Mutations, J. Med. Chem. 2009, 52, 2836-2845; Fujisawa, K., Hoshiya, T., Kawaguchi, H., Aminoglycoside antibiotics. VII. Acute toxicity of aminoglycoside antibiotics, J. Antibiot. 1974, 27, 677-681; and Kondo, S., Hotta, K., Semisynthetic aminoglycoside antibiotics: Development and enzymatic modifications, J. Infect. Chemother. 1999, 5, 1-9. In contrast, when arbekacin was intravenously injected to mice, $LD_{50}$ is approximately 118 mg/kg.

Test Example 3

Expression of Dystrophin

ABK bulk powder, supplied from Meiji Seika Pharma Co., Ltd., was diluted with physiological salt solution (product of Otsuka Pharmaceutical Co., Ltd.) so as to prepare a solution of 1 mg/0.1 mL. The prepared solution was subcutaneously administered daily for 2 weeks to mdx mice, a model animal of Duchenne muscular dystrophy (male and female littermates, 5 months old, n=8). Then, the rectus muscle of the thigh was excised and frozen sections were prepared. The prepared frozen sections were subjected to immunostaining using rabbit polyclonal anti-dystrophin antibody (product of AbCam) as a primary antibody.

Figure 1:
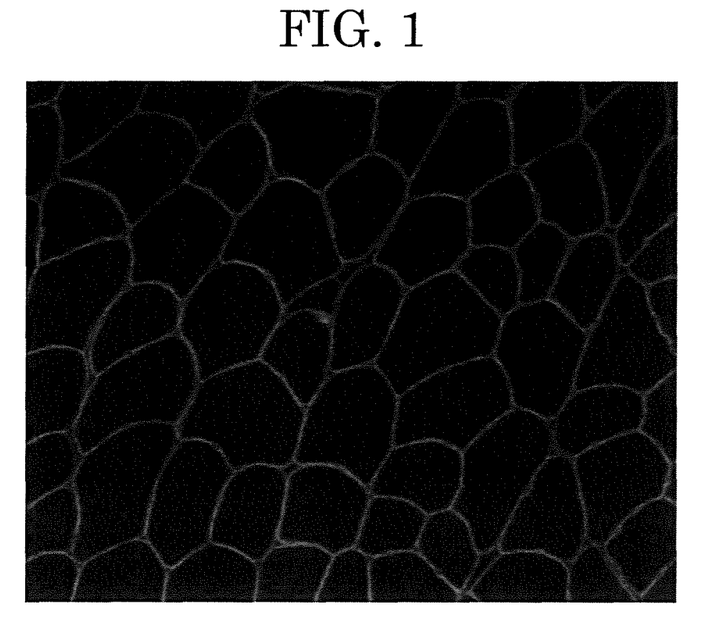
FIG. 1 shows an image of immunostaining of a normal mouse with an anti-dystrophin antibody.
Figure 2:
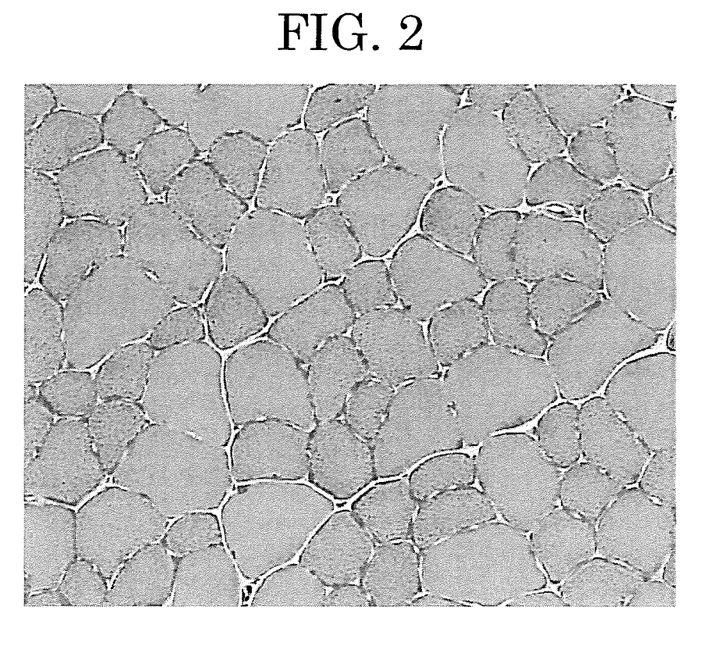
FIG. 2 shows an image of hematoxylin and eosin stain of a normal mouse.
Figure 3:
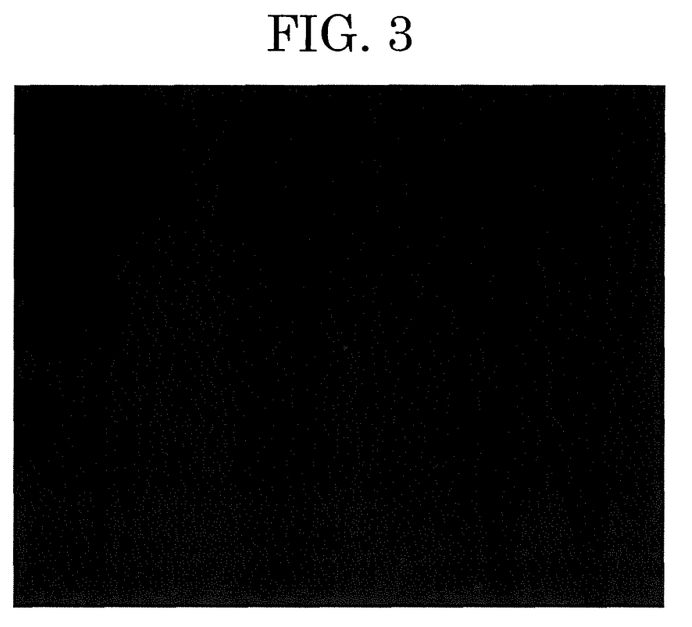
FIG. 3 shows an image of immunostaining of an mdx mouse, to which only physiological saline was administered, with an anti-dystrophin antibody.
Figure 4:
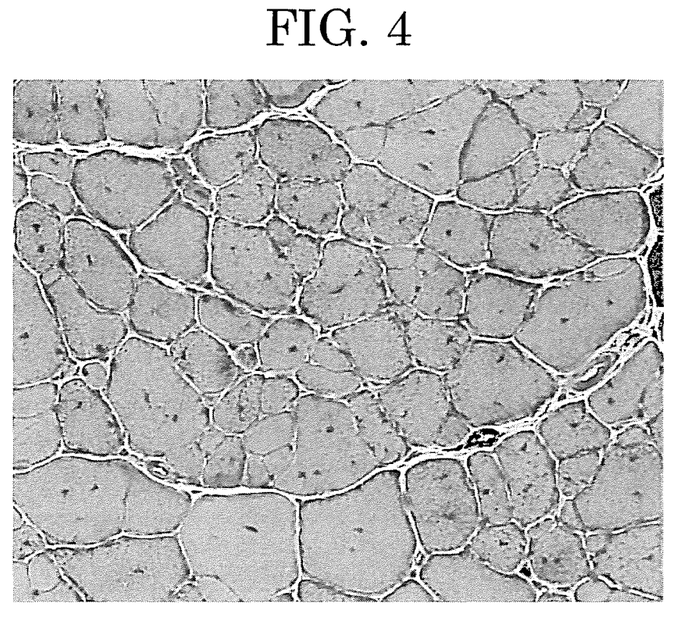
FIG. 4 shows an image of hematoxylin and eosin stain of an mdx mouse to which only physiological saline was administered.
Figure 5:
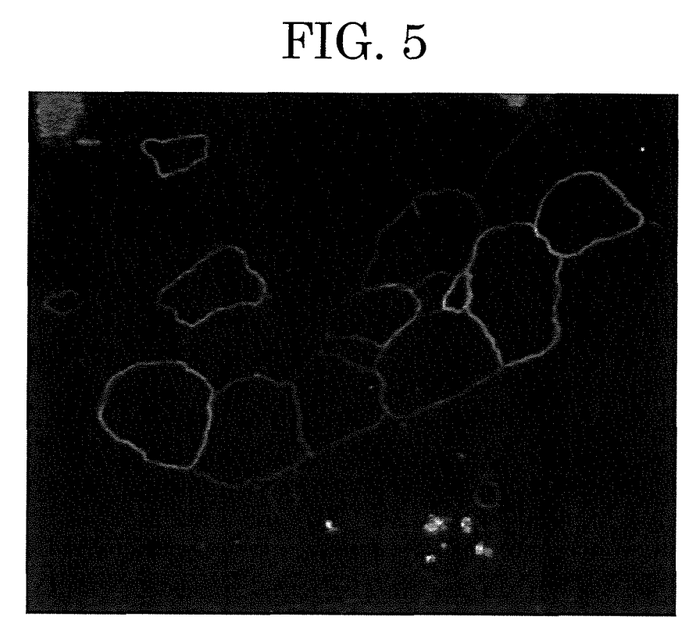
FIG. 5 shows an image of immunostaining of an mdx mouse, to which ABK was administered, with an anti-dystrophin antibody.
Figure 6:
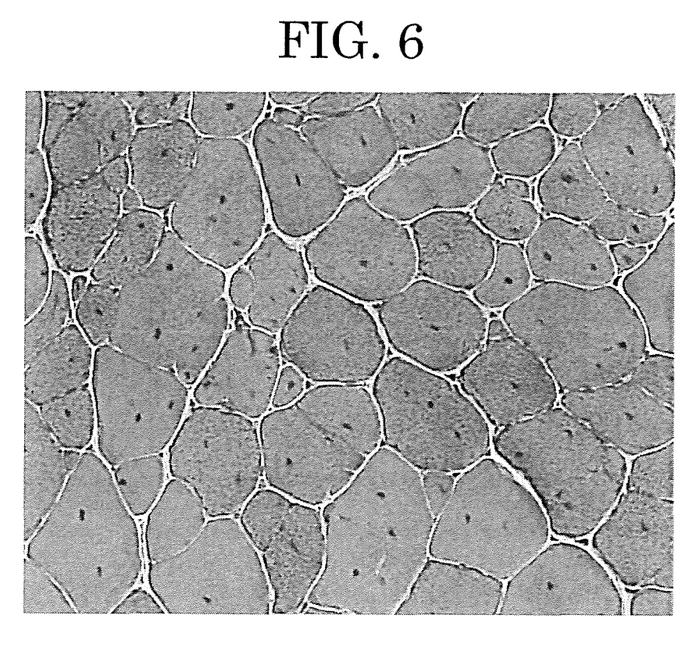
FIG. 6 shows an image of hematoxylin and eosin stain of an mdx mouse to which ABK was administered.

FIG. 1 shows an image of immunostaining of the section from a normal mouse with an anti-dystrophin antibody. FIG. 2 shows an image of hematoxylin and eosin stain of the section from a normal mouse. FIG. 3 shows an image of immunostaining of the section from an mdx mouse, to which only physiological saline was administered, with an anti-dystrophin antibody. FIG. 4 shows an image of hematoxylin and eosin stain of the section from an mdx mouse to which only physiological saline was administered. FIG. 5 shows an image of immunostaining of the section from an mdx mouse, to which ABK was administered, with an anti-dystrophin antibody. FIG. 6 shows an image of hematoxylin and eosin stain of the section from an mdx mouse to which ABK was administered.

As shown in FIGS. 1 and 2, it is found that normal mice express dystrophin and the size of muscle tissue is uniform or homogeneous. In contrast, as shown in FIGS. 3 and 4, it is found that mdx mice do not express dystrophin and the size of muscle tissue is heterogeneous.

As shown in FIGS. 5 and 6, it is found that the mdx mice, to which arbekacin (ABK) was administered, express dystrophin and in addition, the size of muscle tissue is uniform or homogeneous.

Thus, it was confirmed that arbekacin is effective as a therapeutic drug for muscular dystrophy.

Test Example 4

Measurement of Tension of Forelimb

ABK bulk powder, supplied from Meiji Seika Pharma Co., Ltd., was diluted with physiological salt solution (product of Otsuka Pharmaceutical Co., Ltd.) so that ABK is administered at the dose of Table 3 below, to thereby prepare 0.1 mL of solution. The prepared solution was subcutaneously administered daily for 2 weeks to mdx mice, a model animal of Duchenne muscular dystrophy (male and female littermates, 5 months old, n=8). After 2 weeks, tension of forelimb was measured.

The tension of forelimb was measured with a grip strength meter for small animals (force gauge was a product of Japan Instrumentation System Co., Ltd).

In Table 3 below, the tension is expressed as a relative tension where the tension of the forelimb of the normal mice, which is corrected by the body weight, is defined as 100.

TABLE 3

| Compound administered | Dose mg/day | Tension |
|---|---|---|
| None (Physiological saline alone) | | 76.3 (SD = 5.3) |
| ABK | 1 | 87.0 (SD = 3.9) |

The results in Table 3 indicate administration of arbekacin (ABK) restores the tension of the forelimb of the mdx mice. Thus, it was confirmed that arbekacin is effective as a therapeutic drug for muscular dystrophy.

Test Example 5

Measurement of Grip Strength

In the test, the following three groups of mice were used: (1) normal mice, B10 mice (male and female littermates, 5 months old, n=9) (2) mdx mice, a model animal of Duchenne muscular dystrophy (male and female littermates, 5 months old, n=9), to which a diluted solution of habekacin (arbekacin sulfate) was subcutaneously administered at a dose of 1 mg/day daily for 3 weeks; and (3) mdx mice, a model animal of Duchenne muscular dystrophy (male and female littermates, 5 months old, n=8). The diluted solution of habekacin (arbekacin sulfate) was prepared by diluting an injection solution of habekacin (arbekacin sulfate) commercially available from Meiji Seika Pharma Co., Ltd. with physiological salt solution (product of Otsuka Pharmaceutical Co., Ltd.).

As an apparatus for measuring the grip strength, an apparatus was prepared referring to a grip strength meter for small animals by attaching a stainless wire grid with 70 mm long and 55 mm wide to a commercially available force gauge (product of Japan Instrumentation System Co., Ltd). This force gauge has specification: precision: ±0.2% FS, repeat precision: ±0.1% FS, and maximum 100N (10 kgf). The force gauge has a resolution of 1/10,000 of 0.01N (1 gf) and allows peak measurement.

The grip strength of the mice was measured as follows.

A mouse was placed onto the grid for measurement and was pulled by the tail horizontally with a hand. The maximum force (grip strength) was measured when the mouse released the grid, which the mouse gripped, without the mouse being capable of resisting the force pulled. The measurement of the grip strength was repeated five times, with an interval period of 2 minutes between measurements, and the average thereof was calculated. Note that the grip strength measured was normalized by dividing with the body weight.

Figure 7:
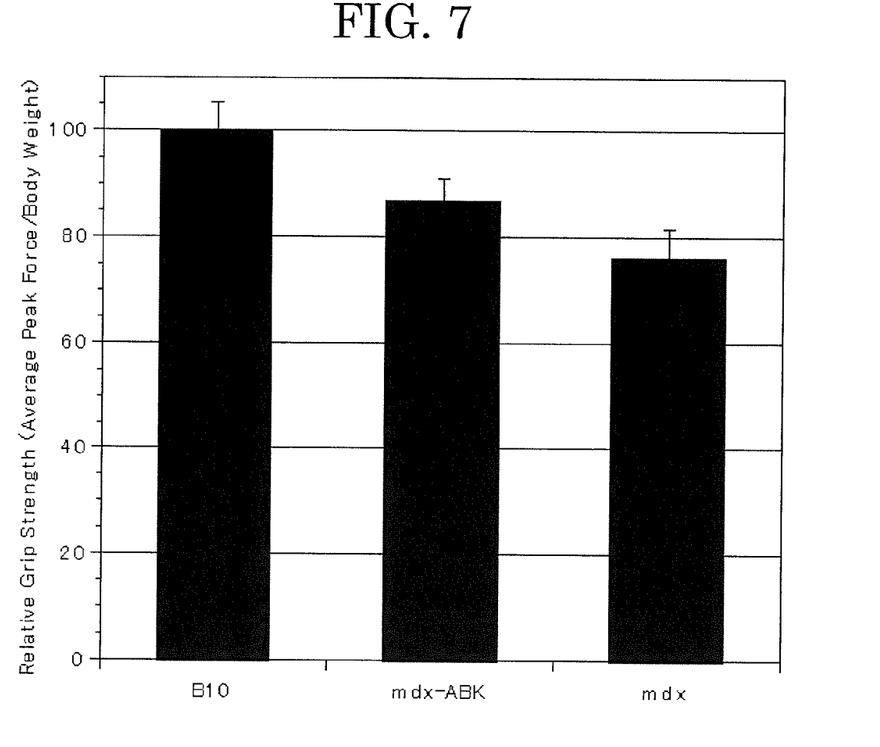
FIG. 7 is a figure showing a result of the measurements of the grip strength in Test Example 5 of the B10 mice, the mdx mice to which arbekacin was administered, and the mdx mice to which arbekacin was not administered.

The results of the measurements of the grip strength are shown in FIG. 7.

In FIG. 7, "B10" represents the result of the (1) normal mice, B10 mice; "mdx-ABK" represents the result of the (2) mdx mice to which arbekacin was administered, and "mdx" represents the result of the (3) mdx mice to which arbekacin was not administered.

From the results in FIG. 7, it was confirmed that administration of arbekacin improves muscle force.

Test Example 6

Measurement of Gastrocnemius Muscle Tetanus Tension

In the test, the following two groups of mice were used: (1) mdx mice, a model animal of Duchenne muscular dystrophy (male littermates, 4 months old), to which a diluted solution of habekacin (arbekacin sulfate) was subcutaneously administered at a dose of 2.5 mg/day daily for 3 weeks; and (2) mdx mice, a model animal of Duchenne muscular dystrophy (male littermates, 4 months old). The diluted solution of habekacin (arbekacin sulfate) was prepared by diluting an injection solution of habekacin (arbekacin sulfate) commercially available from Meiji Seika Pharma Co., Ltd. with physiological salt solution (product of Otsuka Pharmaceutical Co., Ltd.).

The gastrocnemius muscle tetanus tension was measured using a system for measuring isometric contraction tension that consists of a personal computer, an AD/DA converter, an electrode, and a force gauge as follows.

First, the triceps muscle of the calf of a mouse was cut under the anesthesia of Nembutal and the length of the triceps muscle of the calf was measured.

Next, Achilles tendon was cut apart at the calcaneal bone, tied with cotton thread and fitted to a force gauge. Simultaneously, a platinum electrode for electrical stimulation was inserted to the position of the knee and electrical stimulation was given with a neuromuscle electrical stimulator for diagnosis (product of Nihon Kohden Corporation).

Before the measurement of the tetanus tension of the gastrocnemius muscle, the muscle length (length of muscle) and stimulation voltage were adjusted so that maximum isometric contraction tension is obtained. The isometric contraction tension was normalized by a muscle cross-sectional area (calculated using muscle weight, muscle length, and density 1.06 mg/mm$^3$).

Note that in order to prevent the drying of the surface of the triceps muscle of the calf, physiological saline was applied on the surface thereof.

For the measurement of the tetanus tension of the gastrocnemius muscle, stimulation voltage (short rectangular wave of 0.5 ms width) and muscle length that produced the maximum twitch tension were used and the measurement was performed at a frequency of 80 Hz to 100 Hz, 200-ms burst. Note that the produced tension measured was normalized by a muscle cross-sectional area (calculated using muscle weight, muscle length, and density 1.06 mg/mm$^3$).

The stimulation voltage (0 V to 20 V) and the length of muscle were adjusted so that the twitch tension, generated with a single electrical stimulation, is maximized. Note that the length of muscle was measured with a micrometer.

Figure 8:
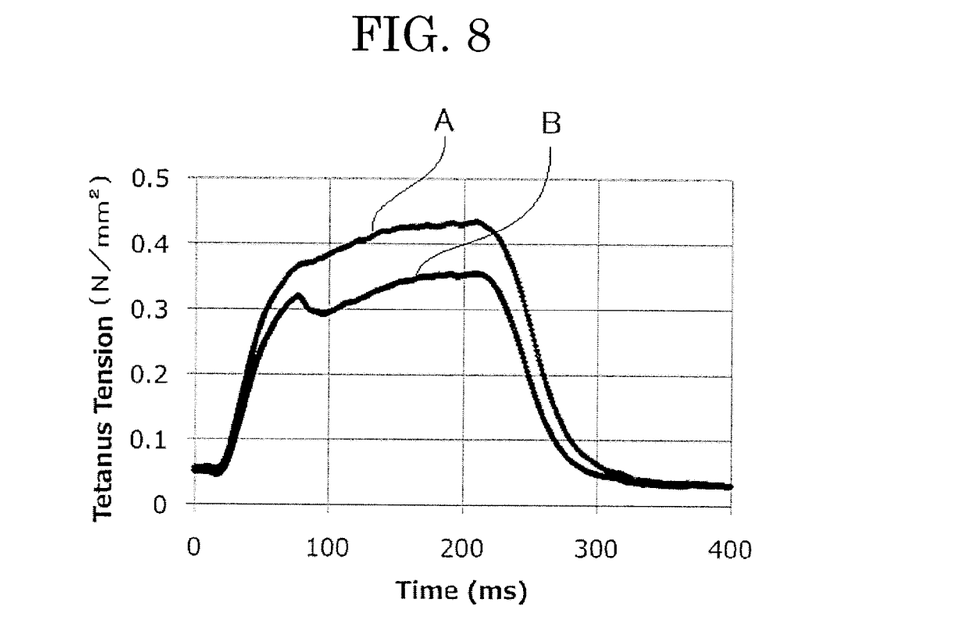
FIG. 8 is a figure showing a result of the measurements of the tetanus tension of the gastrocnemius muscle in Test Example 6 for the mdx mice to which arbekacin was administered and for the mdx mice to which arbekacin was not administered.

FIG. 8 shows the results of the measurements of the tetanus tension of the gastrocnemius muscle.

In FIG. 8, "A" is a result of the mdx mice to which arbekacin was administered, and "B" is a result of the mdx mice to which arbekacin was not administered.

From the results of FIG. 8, it was confirmed that administration of arbekacin improves muscle force.

Test Example 7

Measurement of Gastrocnemius Muscle Twitch Tension

In the test, the following three groups of mice were used: (1) mdx mice, a model animal of Duchenne muscular dystrophy (male littermates, 4 months old), to which a diluted solution of habekacin (arbekacin sulfate) was subcutaneously administered at a dose of 2.5 mg/day daily for 3 weeks; (2) mdx mice, a model animal of Duchenne muscular dystrophy (male littermates, 4 months old), to which a diluted solution of habekacin (arbekacin sulfate) was subcutaneously administered at a dose of 5 mg/day daily for 3 weeks; and (3) mdx mice, a model animal of Duchenne muscular dystrophy (male littermates, 4 months old). Each diluted solution of habekacin (arbekacin sulfate) was prepared by diluting an injection solution of habekacin (arbekacin sulfate) commercially available from Meiji Seika Pharma Co., Ltd. with physiological salt solution (product of Otsuka Pharmaceutical Co., Ltd.).

The twitch tension of the gastrocnemius muscle was measured in the similar manner as in the measurement of gastrocnemius muscle tetanus tension except that electrical stimulation with a short pulse width was given.

Figure 9:
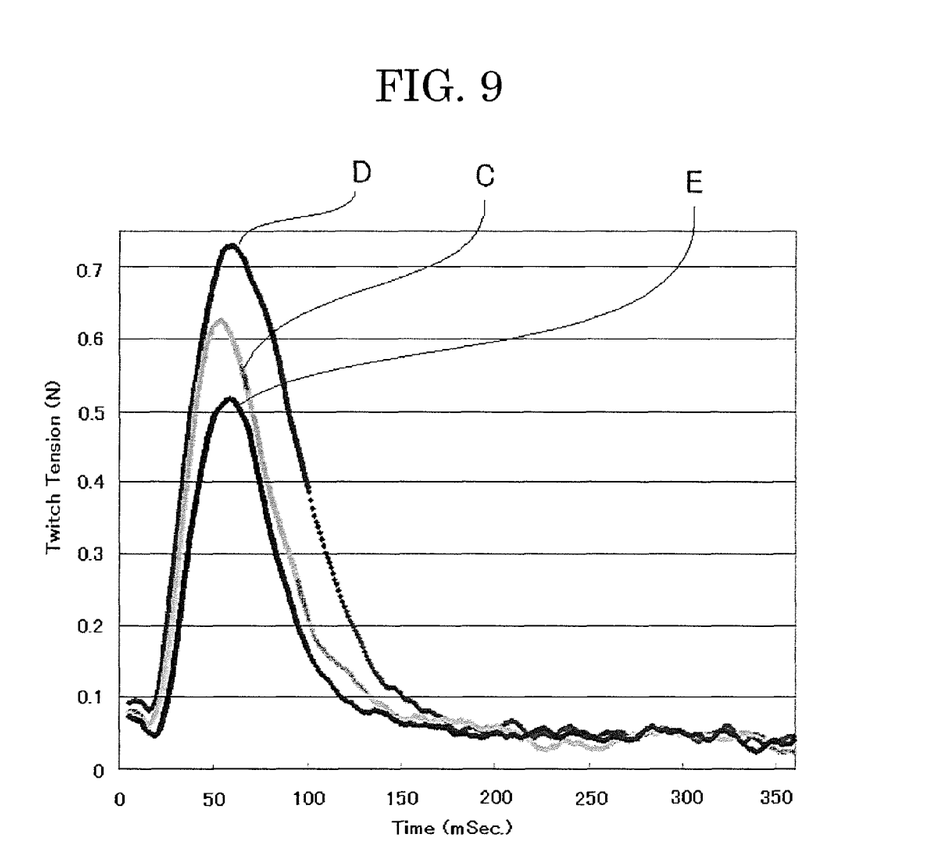
FIG. 9 is a figure showing a result of the measurements of the twitch tension of the gastrocnemius muscle in Test Example 7 for the mdx mice to which arbekacin was administered (2.5 mg/day, 5 mg/day) and for the mdx mice to which arbekacin was not administered.

FIG. 9 shows the results of the measurements of the twitch tension of the gastrocnemius muscle.

In FIG. 9, "C" is a result of the mdx mice (the above (1)) to which arbekacin was subcutaneously administered in an amount of 2.5 mg/day daily for 3 weeks, "D" is a result of the mdx mice (the above (2)) to which arbekacin was subcutaneously administered in an amount of 5 mg/day daily for 3 weeks, and "E" is a result of the mdx mice to which arbekacin was not administered.

From the results of FIG. 9, it was confirmed that administration of arbekacin improves muscle force.

Test Example 8

Expression of Dystrophin in Cultured Muscle Cell Derived from DMD Patient

<Culture of Muscle Cell>

Using two different muscle cells, derived from Duchenne muscular dystrophy (DMD) patients who have nonsense mutations, (#919, #809, both of the muscle cells were derived from the patients having an UAA nonsense mutation), expression of dystrophin in muscle cells derived from DMD patients was examined as follows.

The muscle cells derived from the patients were grown in a growth medium (Dulbecco's modified Eagle minimal essential medium (DMEM, product of Sigma-Aldrich Corporation) containing 20% fetal bovine serum (Gibco), 4% Ultrocer G (Product of Pall Corporation), and 1% Antibiotic-Antimycotic (Gibco) in a gelatin-coated 6 well plate (product of Iwaki Glass Co. Ltd.).

In order to differentiate the cells grown to myotube, the cells were cultured in a differentiation medium (Dulbecco's modified Eagle minimal essential medium (DMEM, product of Sigma-Aldrich Corporation) containing 2% horse serum (Gibco) for two weeks. In the culture, the medium was refreshed and arbekacin (400 μg/mL) was added every two days. In the case of the culture without the addition of arbekacin, only the medium was refreshed. The arbekacin solution used was prepared by adjusting the concentration of the injection solution of habekacin (arbekacinsulfate) commercially available from Meiji Seika Pharma Co., Ltd. to the above concentration.

<Western Blotting>

After the culture, the cells were washed with phosphate buffer saline (PBS). Then, cells were lysed with 1× Cell Lysis Buffer (product of Cell Signaling Technology) and collected. The collected total proteins (for cells without addition of arbekacin: 60 μg, for cells with addition of arbekacin: 30 μg) were loaded on 3%-10% polyacrylamide gel (PAGEL, product of ATTO Corporation). The proteins fractionated with the electrophoresis were transferred to HYBOND-P (product of GE Healthcare).

Western blotting was carried out using ECL advance Western Blotting Detection kit (product of GE Healthcare) according to the manual of the manufacturer. NCL-DYS2 (product of Leica Microsystems) was used as an antibody against the C terminus of dystrophin at a dilution of 1:10, and anti-mouse IgG (product of GE Healthcare) was used for the detection of the dystrophin-anti-dystrophin immune complexes.

In addition, Western blotting for Desmin was performed in the same manner. H-76 (product of Santa Cruz Biotechnology Inc.) was used as an antibody against the Desmin at a dilution of 1:50 and anti-rabbit IgG (product of GE Healthcare) was used for the detection of the Desmin-anti-Desmin immune complex.

Figure 10:
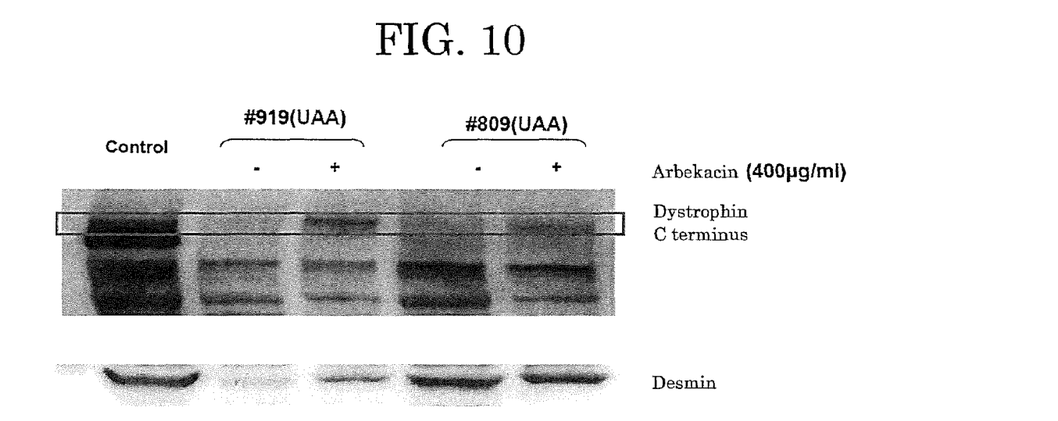
FIG. 10 is a figure showing a result of Western blotting in Test Example 8.

The results of the Western blotting are shown in Table 4 and FIG. 10.

TABLE 4

| Relative expression level of dystrophin/desmin | | |
|---|---|---|
| Cell | Arbekacin | Expression level |
| Control | | 100 |
| #919 | − (W/O addition) | 0 |
| #919 | + (With addition) | 32 |
| #809 | − (W/O addition) | 0 |
| #809 | + (With addition) | 15 |

The results of Table 4 and FIG. 10 indicate that the expression of dystrophin restored in two different cultured cells (#919, #809) derived from the patients having UAA nonsense mutation. By suppressing the premature stop codon, the expression of the dystrophin protein can be induced, thus enabling the alleviation of the muscle damage resulting from muscular contraction in daily living.

Aspects of the present invention are as follows, for example.

<1> A readthrough inducing agent for inducing readthrough of a premature stop codon generated by nonsense mutations, the readthrough inducing agent comprising:
a compound having a structure expressed by the following Structural Formula (A):

Structural Formula (A)

<2> A drug for treating a genetic disease caused by nonsense mutations, the drug comprising:
the readthrough inducing agent according to <1>.
<3> The drug according to <2>, wherein the genetic disease caused by nonsense mutations is muscular dystrophy.

<4> A method for treating an individual having a genetic disease caused by nonsense mutations, the method comprising:
administering to the individual at least one of the readthrough inducing agent according to <1> and the drug according to <2>.

<5> The method according to <4>, wherein the genetic disease caused by nonsense mutations is muscular dystrophy.

<6> The method according to <4> or <5>, wherein a dose of at least one of the readthrough inducing agent according to <1> and the drug according to <2> is, in terms of an amount of the compound having a structure expressed by the Structural Formula (A), 0.1 mg/kg/day to 300 mg/kg/day.

<7> The method according to <4> or <5>, wherein a dose of at least one of the readthrough inducing agent according to <1> and the drug according to <2> is, in terms of an amount of the compound a structure expressed by the Structural Formula (A), 0.5 mg/kg/day to 50 mg/kg/day.

<8> The readthrough inducing agent according to <1>, wherein the readthrough inducing agent is used for treating a genetic disease caused by nonsense mutations.

<9> Use of the readthrough inducing agent according to <1> for the manufacture of a medicament effective in treating a genetic disease caused by nonsense mutations.

The readthrough inducing agent of the present invention contains arbekacin and has low toxicity and excellent readthrough activity. Accordingly, the readthrough inducing agent of the present invention can be suitably used as a drug for treating a genetic disease caused by nonsense mutations.

In addition, arbekacin is approved as a therapeutic drug against infectious disease caused by MRSA. Thus, the drug for treating a genetic disease caused by nonsense mutations of the present invention can be suitably used as a drug for treating a genetic disease caused by nonsense mutations for which keen demand has arisen.

What is claimed is:

1. A method for treating an individual having a genetic disease caused by nonsense mutations, the method comprising:
administering to the individual an effective amount of at least one of a readthrough inducing agent comprising a compound having a structure expressed by the following Structural Formula (A) and a drug for treating a genetic disease caused by nonsense mutations, the drug comprising said readthrough inducing agent,
wherein the genetic disease caused by nonsense mutations is muscular dystrophy:

Structural Formula (A)

2. The method according to claim 1, wherein a dose of at least one of the readthrough inducing agent and the drug for treating a genetic disease caused by nonsense mutations is, in terms of an amount of the compound having a structure expressed by the Structural Formula (A), 0.1 mg/kg/day to 300 mg/kg/day.

3. The method according to claim 1, wherein a dose of at least one of the readthrough inducing agent and the drug for treating a genetic disease caused by nonsense mutations is, in terms of an amount of the compound having a structure expressed by the Structural Formula (A), 0.5 mg/kg/day to 50 mg/kg/day.

4. The method according to claim 1, wherein muscular dystrophy is Duchenne muscular dystrophy.

5. The method according to claim 4, wherein a dose of at least one of the readthrough inducing agent and the drug for treating a genetic disease caused by nonsense mutations is, in terms of an amount of the compound having a structure expressed by the Structural Formula (A), 0.1 mg/kg/day to 300 mg/kg/day.

6. The method according to claim 4, wherein a dose of at least one of the readthrough inducing agent and the drug for treating a genetic disease caused by nonsense mutations is, in terms of an amount of the compound having a structure expressed by the Structural Formula (A), 0.5 mg/kg/day to 50 mg/kg/day.

* * * * *